United States Patent [19]
Gustilo

[11] Patent Number: 6,019,761
[45] Date of Patent: Feb. 1, 2000

[54] INTRAMEDULLARY NAIL AND METHOD OF USE

[76] Inventor: Ramon B. Gustilo, 6541 Beach Rd., Eden Prairie, Minn. 55344

[21] Appl. No.: 09/219,668

[22] Filed: Dec. 23, 1998

[51] Int. Cl.[7] .................................................. A61B 17/72
[52] U.S. Cl. .................................. 606/62; 606/64; 606/96
[58] Field of Search ................................ 606/62, 63, 64, 606/60, 96, 97, 98, 86, 72, 73

[56] References Cited

U.S. PATENT DOCUMENTS

| | | | |
|---|---|---|---|
| 4,981,481 | 1/1991 | Kranz et al. | 606/62 |
| 5,478,343 | 12/1995 | Ritter | 606/97 |
| 5,484,438 | 1/1996 | Pennig | 606/64 |
| 5,713,901 | 2/1998 | Tock | 606/62 |

*Primary Examiner*—Michael Buiz
*Assistant Examiner*—David O. Reip
*Attorney, Agent, or Firm*—Gregory F. Cotterell

[57] ABSTRACT

The present invention is an intramedullary nail (IM nail) device suitable for implanting within a medullary canal of a fractured long bone and subsequently interlocking the IM nail at least once to the cortical bone of the long bone. The IM nail includes a hollow center and at least a proximal opening into the hollow center and an optional distal tip opening. The IM nail is initially manufactured without any holes, channels, or the like, for the alignment and passage of screws or similar devices suitable for interlocking the IM nail with the long bone. The IM nail includes a material suitably adapted for providing post implanting drilling there through and interlocking with the long bone using these post implantation holes. The present invention makes use of removable and expandable first and optional second sealing plugs in operable sealing contact within the hollow center. The present invention also includes a cylindrical sleeve having a hollow bore open at both ends on a longitudinal axis. The cylindrical sleeve is suitable for receiving a drill bit through the hollow bore to act as a drill bit guide. The cylindrical sleeve also includes a resilient gasket at one end suitable for operable sealing engagement with the intramedullary nail outer surface.

35 Claims, 17 Drawing Sheets

INTRAMEDULLARY NAIL AND METHOD OF USE

FIELD OF THE INVENTION

The present invention relates to an improved apparatus and method for the immobilization and fixation of fractures and, in particular, to an improved intramedullary nail and locking procedure for immobilizing bone fractures.

BACKGROUND OF THE INVENTION

Choices for the treatment for fractures of the long bones extend back over a long and complex history. The significant long bones of the extremities are the humerus, radius and ulna of the upper extremity and the femur and tibia of the lower extremity. The upper extremities are considered non-weight bearing while the lower extremities are weight bearing, i.e., normally bearing the weight of the individual. The length of these bones, in conjunction with their inter-articulations, forms the fundamental basis for an individual's ability to generate leverages, or moments of force, that enable the individual to walk, run, use tools and other heavy equipment, and, in general, interact physically with their environment.

At the moment of injury to bones, in particular, injuries resulting in fractures of the long bones, it is the inadvertent application of leverage-like forces over the length of a long bone that is the usual causative factor in fracturing. In general, the weight bearing bones are more difficult to heal and suffer more frequent complications associated with their injuries than the non-weight bearing bones. Additionally, it is well known in medicine that the earlier a patient is mobilized as part of a comprehensive rehabilitation program, the faster they heal, with stronger repair and less likelihood of associated complications. For weight bearing bones, early mobilization carries the added difficulty of providing for sufficiently stabilizing a fractured bone structure to carry weight before there has been adequate healing for the bone to bear that weight.

To reach this goal of early mobilization of the patient, a number of fixation devices, both external and implantable, have been devised over the centuries. These devices accomplish immobilization of the fracture fragments and stabilization of the fractured long bone, providing earlier mobility and weight bearing. Intramedullary (IM) nailing, particularly interlocking IM nailing, has become the standard procedure for immobilizing shaft fractures of long bones including proximal or distal fractures of the weight bearing long bones.

IM nails are available in any number of lengths, widths, cross-sectional shapes, with or without slots, and thickness of wall. A functional aspect common to all IM nails is the close association, a wedging so to speak, of the IM nail and the cortical bone inner wall of the isthmus of the intramedullary canal, also known as the contact area. The more longitudinal and circumferential the contact between the bone and the nail, the more stable the immobilization of the fracture fragments and the less motion that occurs at the fracture site.

Additional stability is achieved using a procedure known as interlocking. Whether an IM nail is also interlocked, and how the interlock is achieved, is dependent on the type of IM nail used, the type of fracture, and the experience of the operator. With this procedure, the IM nail is locked to the bone using either cortical screws or some sort of wing or anchor, depending on the method of interlock proximally, distally, or both. A dynamic lock is achieved when interlocking occurs only between the proximal end of the IM nail and the proximal portion of bone or just between the distal portion of the IM nail and the distal portion of the bone. Consequently, there is a definite potential for motion between the fracture pieces at the fracture site with weight bearing, but this procedure also provides for greater compression between the fracture pieces at the fracture site. Static interlocking involves interlocking the proximal and distal portions of the IM nail to those respective bone fragments, i.e., both the proximal and distal portions of the long bone are locked to the IM nail. With the IM nail bridging the fracture gap and fixated to the proximal and distal bone fragments, the probability of motion at the fracture site is markedly reduced. However, the ability to actively compress the fracture fragments into each other is also attenuated. Using newer compression techniques, the general consensus currently is to rely mostly on static interlocking.

The most common form of interlocking is the cortical bone lock. This procedure uses cortical screws placed through the bone and IM nail, transverse or oblique to the long axis of the bone and IM nail. The screws are first driven through the near wall of bone, then guided through pre-formed holes in the near and far walls of the IM nail, and finished by imbedding into the opposite cortical bone wall. Another form of interlocking is the cancellous bone lock. This interlock uses deployable wings, or anchors, pre-attached to the IM nail, that are deployed into the cancellous bone of the marrow space after the IM nail is positioned. These locks are subcortical in the cancellous bone and because of the loose trabecular nature of cancellous bone, are considerably less stable than cortical locking. For additional discussion concerning IM nails and interlocking, see Bechtold, Joan E., Ph.D., *Chapter 2: Biomechanics of Fracture Fixation Devices* in *Fractures and Dislocations*, volume 1 Gustilo, Ramon B., M.D., Kyle, Richard F. M.D., and Templeman, David C. M.D., editors (Mosby-Year Book, Inc. 1993).

A significant disadvantage to the procedure for cortical interlocking IM nails is placement of the cortical screws through the pre-formed holes of the IM nail. The major difficulty encountered is targeting the distal screw holes. Proximal screw holes are usually easier to locate, particularly with the use of targeting jigs. As the IM nail is inserted into the intramedullary canal, it can twist and deform, therefore, the surgeon cannot readily rely on proximally based targeting jigs for the placement of the locking screws through the distal holes.

Therefore, the generally accepted technique currently is to use x-rays and an x-ray image intensifier built into a C-arm apparatus. The image is provided through a fluoroscopic video in real time. The C-arm is positioned so that the central axis of the x-ray bean is collinear with the central axis of the distal screw holes. This shows up as aligned screw holes without parallax. An incision is then made over the position of the IM nail holes and the bone surface is marked on the path of the alignment. A small hole is usually drilled freehand into the near wall of bone to reach the near side pre-formed hole in the IM nail with the purpose of confirming accuracy. If placement is adequate, the hole in the bone is widened sufficiently to accommodate a screw that is inserted through the widened hole and ultimately embedded within the cortical bone.

Using x-rays, while relatively easy, does have complications and significant drawbacks. One such drawback is that the cumulative dose of x-ray radiation to the surgeon and other health care providers may become large over time.

Another is that the technique is not foolproof, erratic screw placement occurs as well as missing distal holes entirely. If a hole is missed, more drilling is required, usually in a new site or by widening the first hole, both of which weaken the bone. Another drawback is the cost and availability of the C-arm and imaging apparatus making this a cost prohibitive procedure in under-developed countries.

There exists a distinct need for an interlocking IM nail and method that does not need to rely on x-ray imaging, extraneous alignment jigs or pre-formed screw holes. An improved IM nail and method would continue to use cortical screws in either a dynamic or a static interlocking IM nail fixation.

There is a need for an intramedullary nail device that will substantially reduce, if not eliminate many of the difficulties encountered with current intramedullary nails and other fixation systems. Such a device and method would provide appropriate fixation and stabilization without the need for x-ray radiation methods of alignment, eliminating the risk of excess exposure to x-ray radiation, without excess loss of good bone stock, that is easy to implant and interlock, and is substantially cheaper to manufacture.

SUMMARY OF THE INVENTION

The present invention is an intramedullary nail (IM nail) device suitable for implanting within a medullary canal of a fractured long bone and subsequently interlocking the IM nail. The interlocking of the IM nail to the cortical bone of the long bone may be achieved at least once using at least one screw or at least one Kirschner wire (K wire) tensioned transversely to obliquely across the bone and IM nail. The intramedullary nail device comprises an intramedullary nail that is preferably roughly circular in cross-section and elongated in a longitudinal axis, although any number of cross-sectional shapes is anticipated by the present invention, including a cloverleaf. The IM nail includes either at least a portion of its length where it is drilled is solid or has a hollow center and at least a proximal end opening communicating into the hollow center and an optional distal tip opening. An alternative embodiment uses a cortical screw for completing the interlocking.

An important feature of the IM nail of the present invention is the material forming the wall of the IM nail. The IM nail of the present invention is manufactured without any holes, channels, or the like, in the distal portion of the IM nail that are usually reserved for passage of screws or similar securing devices suitable for interlocking the IM nail with the long bone. Instead, the IM nail of the present invention includes a wall suitably adapted for providing post implanting drilling there through, and interlocking with the distal long bone using tensioned K wires or cortical bone screws passing through these post implantation drilled holes.

For the hollow IM nail, the present invention makes use of a removable and expandable first plug in operable sealing contact to the inner wall of the IM nail within the IM nail hollow center. The first sealing plug is positionable to a selectable longitudinal axial first position proximate the distal tip of the IM nail. There is also an optional removable and expandable second sealing plug positionable to a selectable longitudinal axial second position proximal to the first sealing plug. The first and second sealing plugs serve a valuable purpose in providing a sealed cavity within the hollow center of the IM nail within which to collect metal turnings produced from the drilling. When present, the second sealing plug is removable and the confined metal turnings are accessible for easy extraction using irrigation and suctioning with the first sealing plug preventing migration of the turnings out the distal tip opening of the IM nail.

The present invention includes a cylindrical sleeve having a hollow bore open at both ends of the sleeve on its longitudinal axis. The cylindrical sleeve is suitable for receiving a drill bit through the hollow bore and to act as a drill bit guide. The cylindrical sleeve includes a resilient gasket at one end suitable for operable sealing engagement with the intramedullary nail outer surface.

A hole is drilled through the cortical bone wall to the IM nail. When the cylindrical sleeve is placed in this hole, the cylindrical sleeve operably seals against the outer wall of the IM nail. The cylindrical sleeve acts as a drill bit guide for the drilling of a hole through the near wall of the IM nail, which will have its longitudinal axis aligned with the cylindrical sleeve. This same alignment is maintained to sequentially drill a hole in the far wall of the IM nail and then the far wall of the cortical bone. Thus all the holes are created using the initial cortical bone hole for aligning all of the subsequent holes.

For an IM nail that has a solid core, the basic concept is the same, first a hole is drilled through the cortical bone wall to the IM nail. The cylindrical sleeve may be placed in this hole operably sealing against the outer wall of the IM nail. The cylindrical sleeve, when used, acts as a drill bit guide for the drilling of a hole through the IM nail and the far wall of cortical bone. The cylindrical sleeve is optional because it is not necessary if the inner wall of cortical bone is abutting the outer surface of the IM nail. The inadvertent migration of metal shavings into the intramedullary canal is not apparent when these two surfaces are in contact.

The present invention also optionally includes at least two removable resilient stoppers suitable for placement in at least two holes drilled into the opposing near and far walls of the IM nail. These resilient stoppers are intended to temporarily operably seal the at least two holes.

Having provided for the post implanting drilling of at least two holes, i.e., a hole in the near cortical bone wall in alignment with a hole in the wall of the IM nail, and each of these holes in alignment with associated cortical bone holes, the present invention anticipates the use of components for completing the interlocking. These components are suitable for passing through the at least two holes drilled into the intramedullary nail and interlocking the intramedullary nail to the long bone cortex.

Suitable interlocking components include several alternatives. These components include involving the use of a K wire in combination with some sort of K wire fixation means. The first is a K wire having a metal bead crimped to the wire at one end or manufactured onto the wire by soldering, welding or brazing, collectively identified as an "olive" wire. Alternatively, one end of the wire may end in a pan head similar to the head of a screw. These types of wires are intended, after positioning across the holes, to then be placed under tension and interlocking across the bone and IM nail by affixing or attaching another component onto the wire abutting the surface of the bone to hold the tension on the wire.

One type of component could be crimping a metal bead onto the wire at the opposite side of the long bone. Another method is to use a K wire having screw threads and using a nut, with or without a washer to lock the wire in place. Other devices contemplate a K wire threaded at both ends using nuts and washers to either side of the long bone to apply and hold tension on the K wire.

The present invention anticipates a method for interlocking an IM nail implantable within a medullary canal of a patient's fractured long bone comprising the following steps. First, providing adequate surgical access to the long bone surface. Then providing an IM nail having a hollow center aligned along a longitudinal axis. The IM nail optionally has at least one removable and expandable sealing plug in operable sealing contact within the hollow center, with at least an first sealing plug proximate a distal tip of the intramedullary nail, and an optional second sealing plug proximal to the first sealing plug.

Next is the step of implanting the intramedullary nail into the medullary canal of the long bone. This step is followed by selecting a point along the fractured long bone. The selected point is suitable for achieving cortical interlocking and fracture fixation. A first drill bit is used to drill a first hole through a near wall of the cortical bone at the selected point in a plane substantially transverse to the longitudinal axis at an axial level proximal to the at least first sealing plug. Then comes the step of optionally providing a cylindrical sleeve, with a hollow bore including a resilient gasket at one end of the sleeve, inserting the cylindrical sleeve into the first hole so as to position the resilient gasket in operable sealing contact with an outer surface of a near wall of the intramedullary nail. Next, using a second drill bit passing through the cylindrical sleeve and drilling a second hole through the near wall of the intramedullary nail along the axis of the first hole. Followed by then cleaning this first hole by irrigating the cylindrical sleeve and second hole with a liquid and suctioning the liquid from the cylindrical sleeve and second hole. Placing the second bit again into the cylindrical sleeve and drilling a third hole through a far wall of the intramedullary nail and cortical bone opposite the second hole. The cylindrical sleeve is removed, then plugging the second and third holes with first and second resilient stoppers. The second sealing plug, when present, is then removed from the hollow center of the intramedullary nail. The hollow center, down to the first sealing plug is cleaned by irrigating the hollow center of the intramedullary nail with a liquid. The liquid is then suctioned from the hollow center of the intramedullary nail. Next, the first sealing plug and the first and second resilient stoppers are removed.

An interlocking device, i.e. a screw or K wire, suitable for passing through the first, second, and third holes, is provided, interlocking the intramedullary nail to the long bone. Interlocking is accomplished by passing the interlocking device through the first, second and third holes and securing the interlocking device at the outer surfaces of the near and far walls of the cortical bone. These steps may be repeated at any number of levels along the longitudinal axis of the IM nail, beginning by replacing both the first and second sealing plugs into the hollow center with the first sealing plug adjacent and proximal to the last placed interlocking device.

The present invention significantly reduces the cost of manufacture of an IM nail by not requiring an IM nail to have pre-drilled holes, slots, grooves, channels, or wings. The present invention also provides for the custom placement of one or more interlocking devices at various levels along the length of the IM nail. Placement may be achieved without any restriction to placement of interlocking screws at predetermined positions. This custom placement provides for the surgeon to be able to adjust placement of an interlock at angles that are not available when using pre-formed IM nails with interlocking holes already defined.

Additionally, the present invention provides the previously unrecognized advantage of placing an interlock even through one or more fracture fragments of a comminuted fracture. This custom placement, particularly through free fracture fragments, significantly improves the stability of the fracture, reducing healing time, providing for a stronger repair and reducing overall the incidence of complications associated with these most difficult of fractures.

The present invention also has the added benefits of avoiding exposure to x-ray radiation, no jigs or other devices are needed to implant, align, and interlock as may be required with IM nails of other systems. Overall, time of operating is also reduced because these other aligning devices or techniques are not needed, a significant benefit to the patient in terms of overall health, as well as cost.

These and other objects of the present invention and many of the attendant advantages of the present invention will be readily appreciated as the same become better understood by reference to the following detailed description when considered in connection with the accompanying drawings.

DETAILED DESCRIPTION OF THE INVENTION

Figure 1:
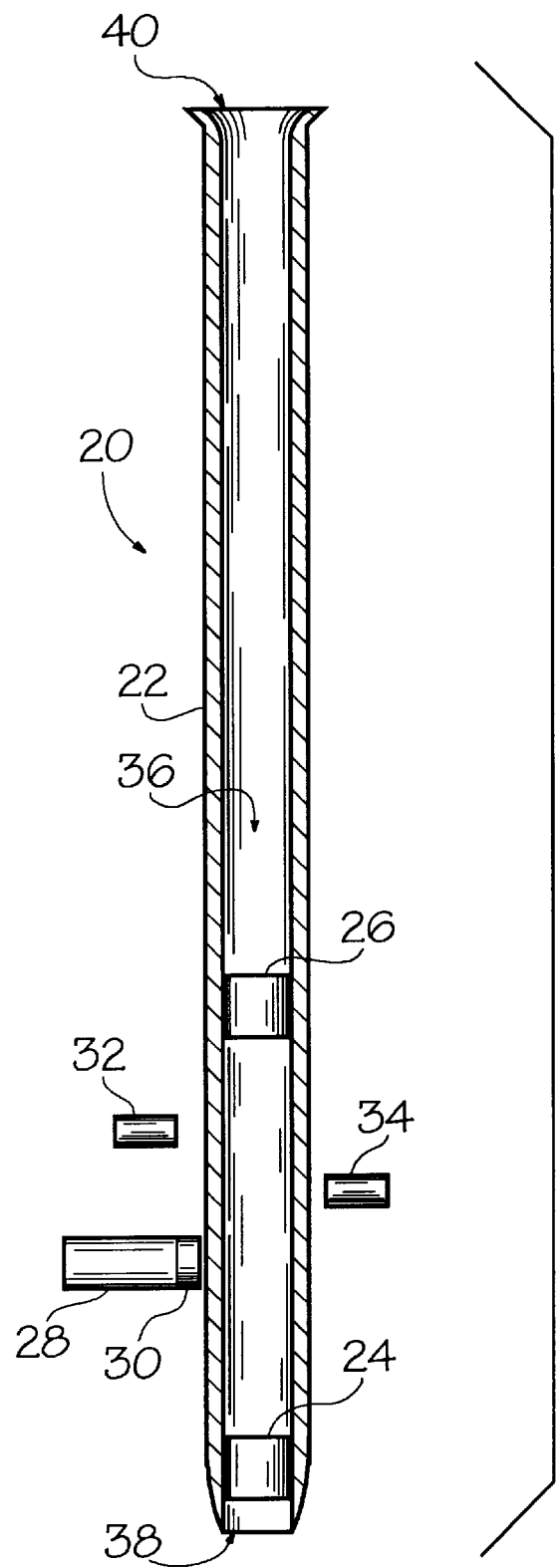
FIG. 1 is an elevational cross-sectional view of an embodiment of the present invention.

In reference to FIGS. 1–13, wherein like reference numbers refer to like components throughout the Figures, there is disclosed an interlocking intramedullary nail device 20 including an intramedullary nail 22 (IM nail 22), a first sealing plug 24, a second sealing plug 26, a cylindrical sleeve 28, a resilient gasket 30, a first resilient stopper 32, and a second resilient stopper 34. IM nail 22 includes a hollow center 36 found generally along the longitudinal axis of IM nail 22 having a distal end 38 and a proximal end 40.

Figure 2:
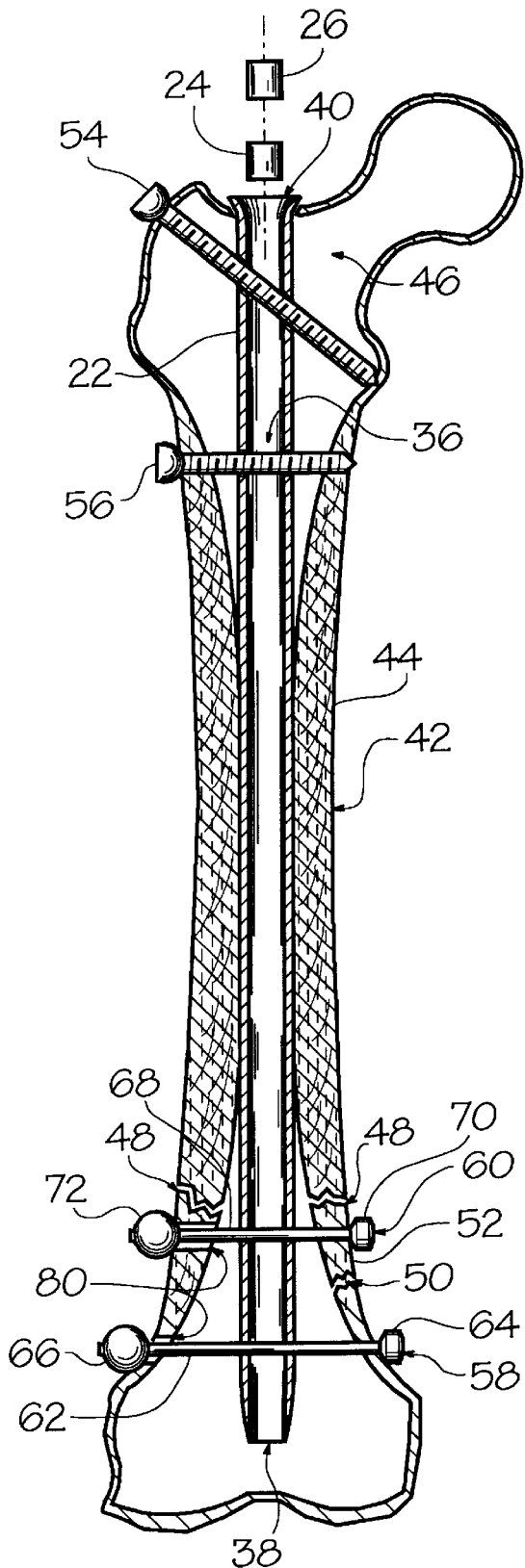
FIG. 2 is a front elevational cross-sectional view the embodiment of FIG. 1 following implantation and interlocking in a patient's femur according to the present invention.
Figure 3:
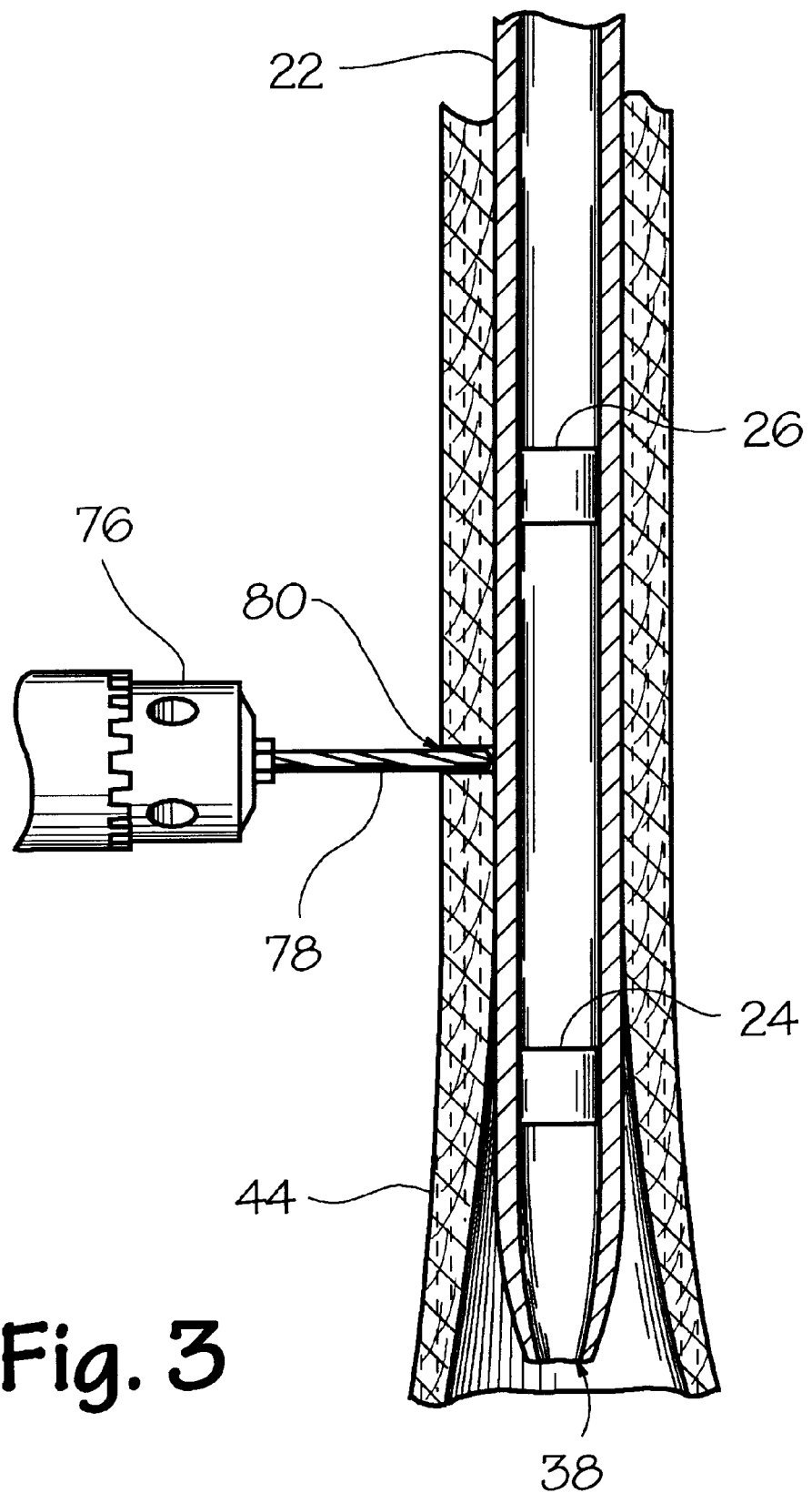
FIG. 3 is a side elevational view of a partial cross-sectional view taken at 3—3 of FIG. 1 wherein the more proximal portion of the intramedullary nail and patient's femur is not shown, the view depicting a step in one embodiment of the present invention.

As depicted in FIG. 2, IM nail 22 has been implanted in a femur 42, generally shown, with a shaft 44 comprising cortical bone and a medullary cavity 46 comprised mostly of cancellous bone, as well as, bone marrow components. Additionally, for illustrative purposes, there is depicted fracture sites 48, 50 defining a fracture fragment 52 there between. In FIG. 2, IM nail 22 is shown in the completed implantation and interlocked orientation having been interlocked with proximal interlocking screws 54, 56, a first distal interlocking wire 58, and a second distal interlocking wire 60. Interlocking wire 58 includes a Kirschner wire (K wire) 62 having an olive 64 at an end opposite a ball 66 that has been crimped in place. Interlocking wire 60 includes a Kirschner wire 68 having an olive 70 at one end opposite a ball 72 crimped onto the other end of Kirschner wire 68.

Intramedullary nail 22 may include any number of different biocompatible metals and metal alloys incorporated into its structure. These biocompatible materials must necessarily be consistent with having the appropriate strength and durability to accomplish their intended task. Examples of acceptable metals and metal compounds are surgical grade stainless steel, although other alloys, such as vitallium, titanium, and cobalt chrome alloy are anticipated by the present invention.

As depicted in the several Figures, IM nail 22 is generally cylindrical in shape with a uniform cylindrical bore shown as hollow center 36. The present invention anticipates that other shapes are available for use as an intramedullary nail of the present invention. Other intramedullary nails may have more complex shapes such as a three-leaf clover shape on cross-section, or curves in either the antero-posterior or medio-lateral directions, and longitudinal scalloping to minimize drill bit skiving, as well as several different types of proximal and distal tapering. The present invention also anticipates that useful intramedullary nails may also include slots in the wall of the intramedullary nail of variable length, generally in the longitudinal direction. Obviously, as different shapes and thicknesses are chosen for use with the present invention, first sealing plug 24 and second sealing plug 26 would also be adapted in shape to conform to and readily fit and operably seal within, the hollow center of the chosen intramedullary nail. An additional aspect of first and second sealing plugs 24, 26 is the usefulness of using expandable plugs that would facilitate placement as well as removal of the sealing plug to and from the hollow center of the intramedullary nail.

Like the choices for an intramedullary nail, the construction of suitable sealing plugs 24, 26 preferably uses a compressible and expandable, resilient material. The material may be from natural rubbers and/or including a number of synthetic elastomeric polymers. The need for selecting biocompatible compounds for use in the construction of the sealing plugs is not as high a priority as the need for biocompatibility of the materials used in the intramedullary nail. The present invention does not anticipate that either sealing plug 24 or 26 will remain in the hollow center of an intramedullary nail after implanting the nail within a long bone, although, with biocompatible materials this is less of a concern. However, the utility of the sealing plugs must always take into account potential toxicity when choosing appropriate compounds for their construction. Numerous medical grade, biocompatible elastomeric compounds are known to the arts, including hard elastomer silicone and polyurethanes.

Figure 4:
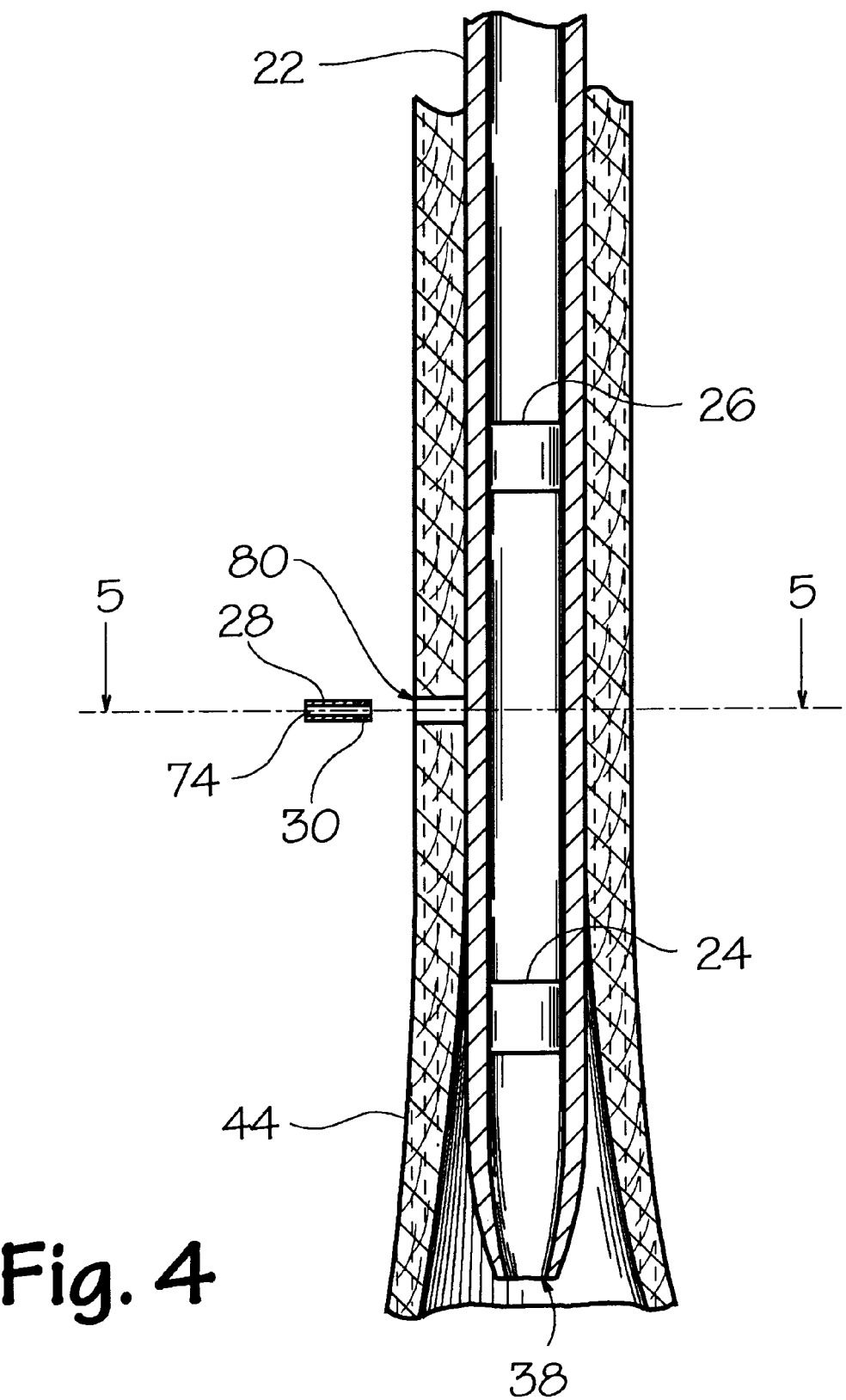
FIG. 4 depicts a next step in the embodiment of FIG. 3.
Figure 5:
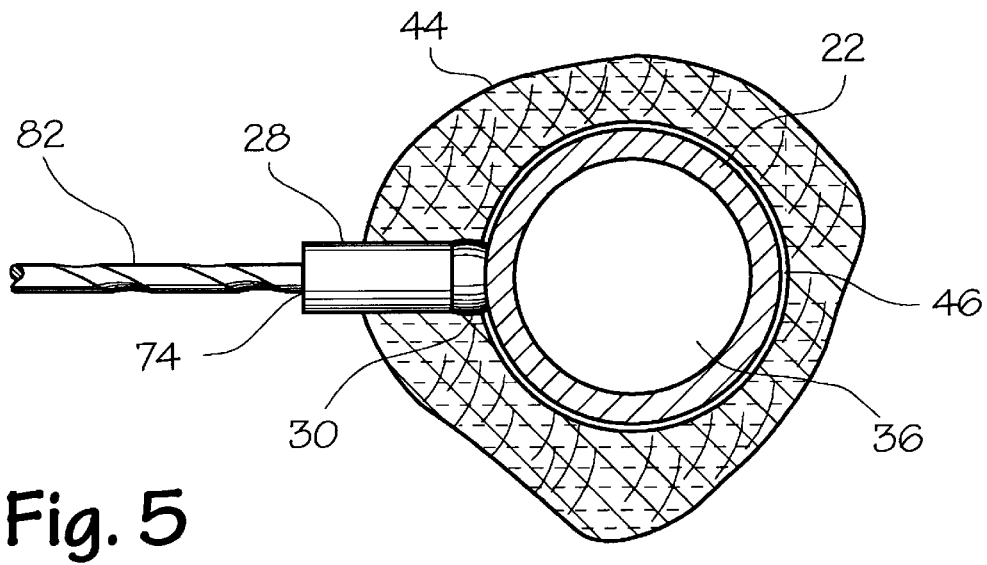
FIG. 5 is a cross-sectional view of the embodiment taken at line 5—5 of FIG. 4 and depicts a next step in the embodiment of FIG. 4.

Cylindrical sleeve 28, in conjunction with resilient gasket 30, is intended as a hollow cylinder with a longitudinally oriented central bore 74, as shown in FIG. 4. Composition of materials for constructing cylindrical sleeve 28 and/or resilient gasket 30 is important only to the extent that the material be strong enough to withstand the general forces associated with pushing the component into a drilled hole in the cortical bone of a long bone such as femur 42. The intended purpose for cylindrical sleeve 28 is to act as a drill guide, as well as participate in cleaning steps involved in the method of the present invention. Resilient gasket 30 serves the function of removably operably sealing cylindrical sleeve 28 to the outer wall of intramedullary nail 22 to prevent the migration of metal shavings into medullary cavity 46 of long bone 42. Preferably, resilient gasket 30 would include, at a minimum, a non-toxic elastomeric polymer, more preferably a biocompatible elastomeric polymer, such as hard elastomer silicone or polyurethane.

The present invention anticipates the use of interlocking the intramedullary nail to the cortical bone. In FIG. 2, there is depicted a set of two proximal interlocking screws 54 and 56. In addition, there is shown a pair of distal interlocking wires, discussed below. Proximal interlocking screws 54, 56 are shown as cortical screws with interlocking screw 54 placed obliquely through intramedullary nail 22 passing from the region of the greater trochanter, superiorly and laterally, to the lesser trochanteric region of the femur, inferiorly and medially. This is a cortical locking because the screw engages and relies on its locking strength from the screw engaging the cortical bone 44 of long bone 42. The same characterization is true of interlocking screw 56, although this interlocking screw is shown in nearly a transverse position at a level consistent with the junction between the metaphysis and diaphysis regions of long bone 42. The choice of cortical screws for use as interlocking screws 54, 56 are well known in the art leaving a practitioner the choice of different metal alloys, thread pitch, as well as width, length, and head size, of the screws.

As depicted in FIG. 2, the present invention anticipates the use of distal cortical bone intramedullary nail interlocking. There is depicted a set of two distal interlocking wires 58, 60. Preferably, these wire devices comprise Kirschner wires 62, 68 (K wires) with pre-formed olives 64, 70 toward one end of K wires 62, 68. Each distal interlocking device 58 and 60 is locked in place with balls 66, 72, respectively, crimped onto their respective wires after the K wire is placed under a distraction tension. K wires with olives and crimping balls represent only a preferred choice, there being a number of different choices available to one skilled in this art. Alternative devices may employ threaded wires and the application of one or more nuts in conjunction with washers or replacing one nut and washer with a pan head to achieve abutment against the cortical bone surface.

In use, intramedullary nail device 20 is implanted into an intramedullary cavity of a long bone by a surgeon after having first obtained adequate surgical exposure of either the proximal and/or distal aspects of the long bone in question. The choice of intramedullary nail may be predicated on the type of fracture encountered, i.e., in terms of whether the fracture is proximal, distal or in the middle of the long bone shaft. Other factors involved are the degree of comminution and/or the absence of bone fragments from the fracture site.

After appropriate surgical access to the long bone, intramedullary nail 22 is driven through the medullary cavity 46 to traverse the fracture site. Ideally, the length of the intramedullary nail is chosen to substantially traverse the entire length of the medullary cavity. In the next step, shown in FIG. 3, a drill 76 with associated drill bit 78 is used to create a first hole 80 in a near wall of cortical bone 44. As shown in FIGS. 3–10, a single interlocking wire is implanted at a distal site. The axial level at which first hole 80 is drilled is chosen to be at a level between first sealing plug 24 and optional second sealing plug 26. The width of drill bit 78 is chosen to provide a conveniently sized hole 80 through which to complete this interlocking procedure.

First sealing plug 24, and second sealing plug 26 when used, may be positioned within the hollow center of the IM nail using a number of different means. Examples are the use of a long hook or screw that is releasable from the body of first and second sealing plugs 24, 26. An optional device and method is discussed below in conjunction with FIGS. 11 and 12.

As shown in FIG. 4, drill bit 78 is removed and cylindrical sleeve 28, with a resilient gasket 30, is placed into hole 80. The outer diameter of cylindrical sleeve 28 and resilient gasket 30 should very nearly match the internal diameter of hole 80. A close-up cross-sectional view in FIG. 5 demonstrates how a second bit 82 is placed through central bore 74 of cylindrical sleeve 28 acting as a drill bit guide. Drill bit 82 is then used to drill a second hole 84 (shown in FIG. 8) to communicate with hollow center 36 of intramedullary nail 22.

Figure 6:
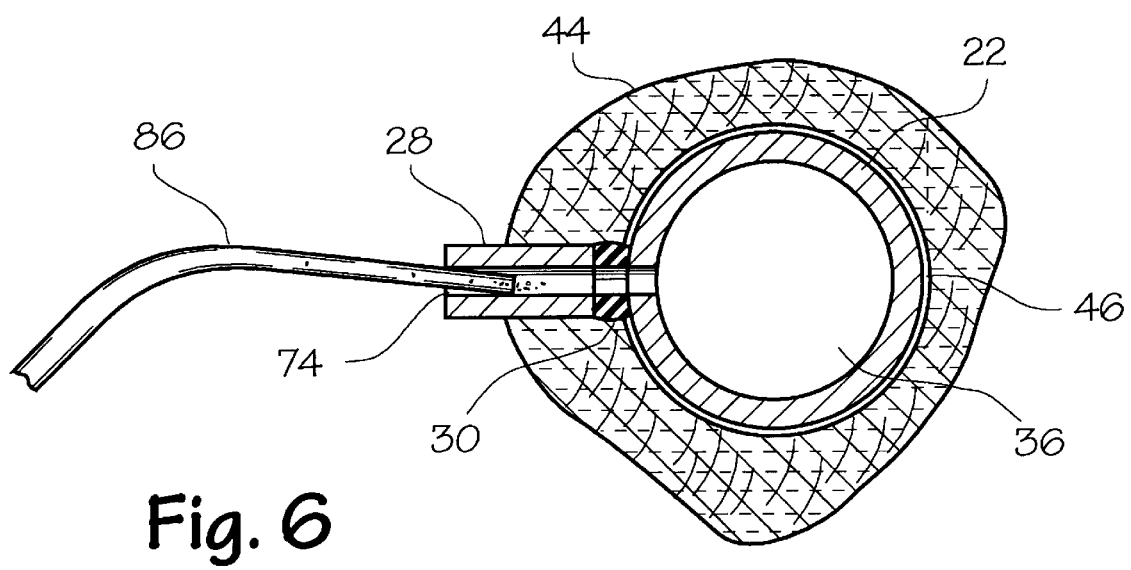
FIG. 6 depicts a next step in the embodiment of FIG. 5.
Figure 6A:
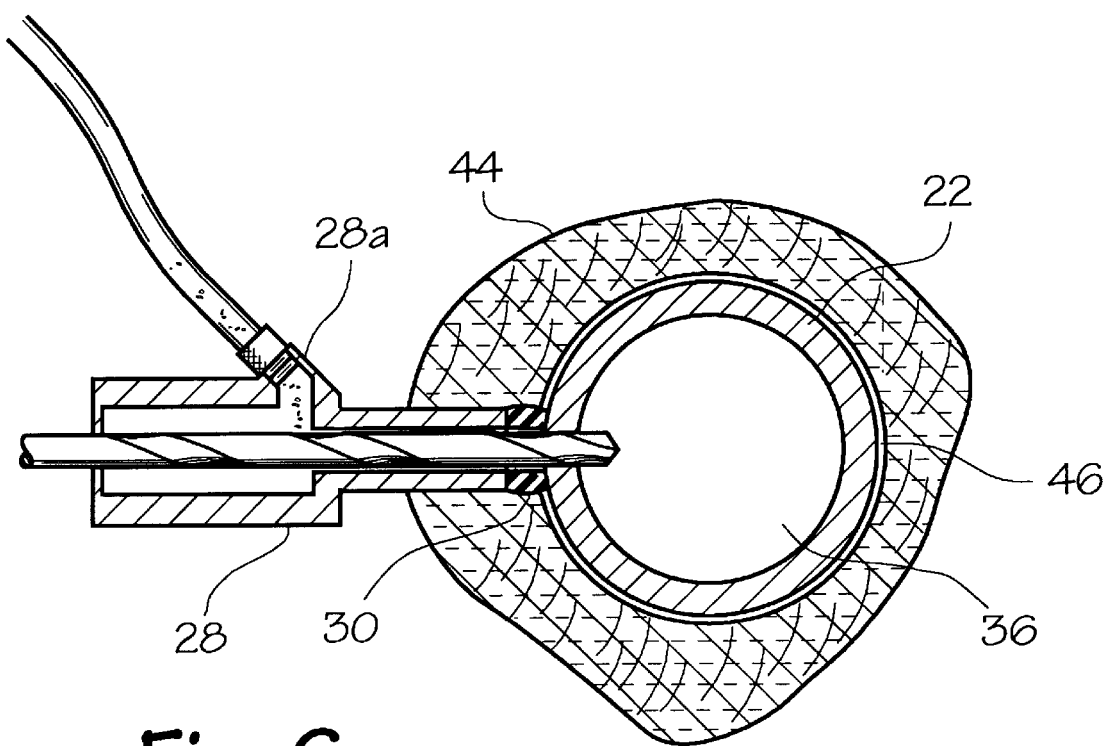
FIG. 6a depicts the step of FIG. 6 with an alternative configuration.

Drill bit 82 is then temporarily removed from cylindrical sleeve 28, as shown in FIG. 6. Irrigation and suction aspiration is carried out with a suction device 86 to completely remove any metallic debris from second hole 84 and central bore 74 prior to removing cylindrical sleeve 28 and resilient gasket 30 from first hole 80. Alternatively, suction and irrigation may be carried out concurrently using a side port 28*a* on cylindrical sleeve 28, as depicted in FIG. 6*a*. This irrigation and suction step ensures that there will not be any metallic debris left to migrate into medullary space 46 or first hole 80. What debris that may have fallen into hollow center 36 will be removed at a later step.

Figure 7:
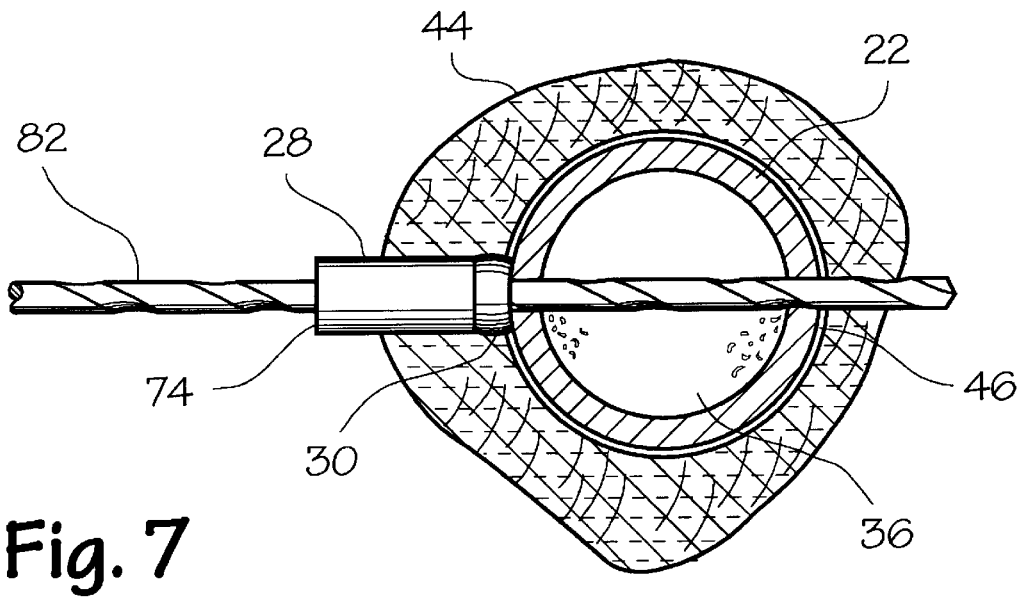
FIG. 7 depicts a next step in the embodiment of FIG. 6.
Figure 8:
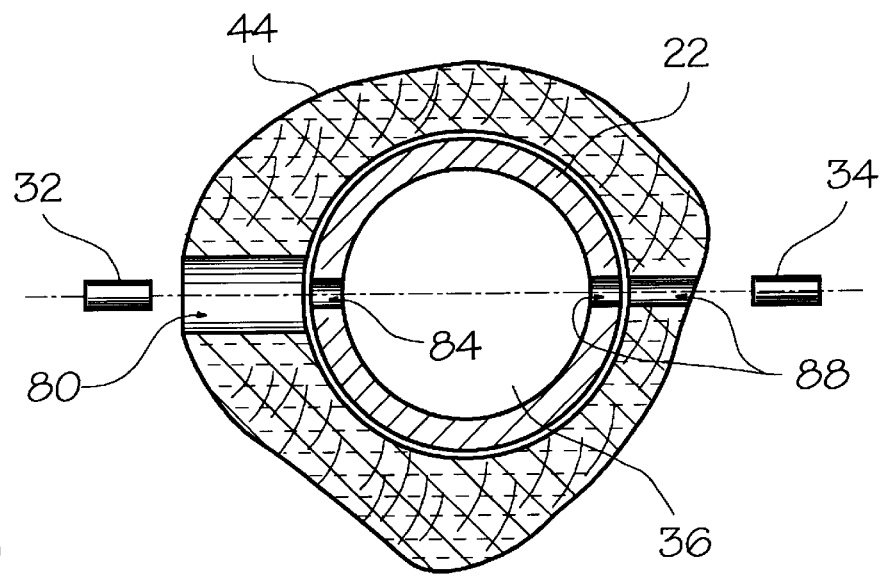
FIG. 8 depicts a next step in the embodiment of FIG. 7.
Figure 9:
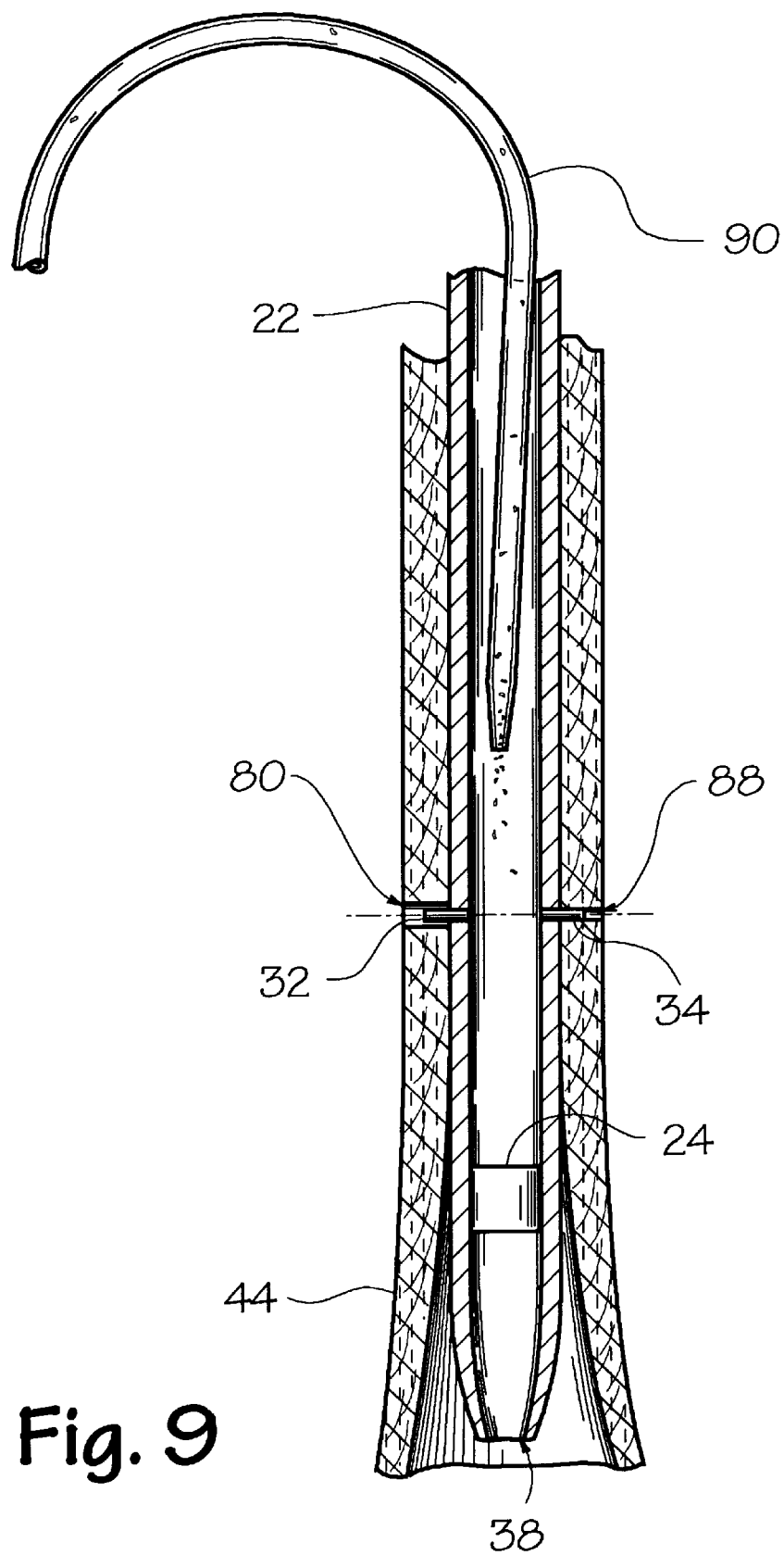
FIG. 9 is a side elevational view of a partial cross-sectional view of a distal aspect of the embodiment of FIG. 1 depicting a next step in the embodiment of FIG. 8.

Drill bit 82 is returned to central bore 74 and, through second hole 84, used to complete the drilling process by drilling a third hole 88. Third hole 88 is a through-and-through hole in the far wall of intramedullary nail 22 and far wall of cortical bone 44, as shown in FIG. 7.

After drill bit 82 is removed, first resilient stopper 32 is placed through hole 80 to seal into second hole 84. Second resilient stopper 34 is placed into third hole 88 to seal third hole 88, shown in FIGS. 8 and 9. With second hole 84 and third hole 88 sealed, a suction device 90, adapted for use within hollow center 36, is then used to irrigate and suction hollow center 36 after second sealing plug 26 has been removed from hollow center 36.

Figure 10:
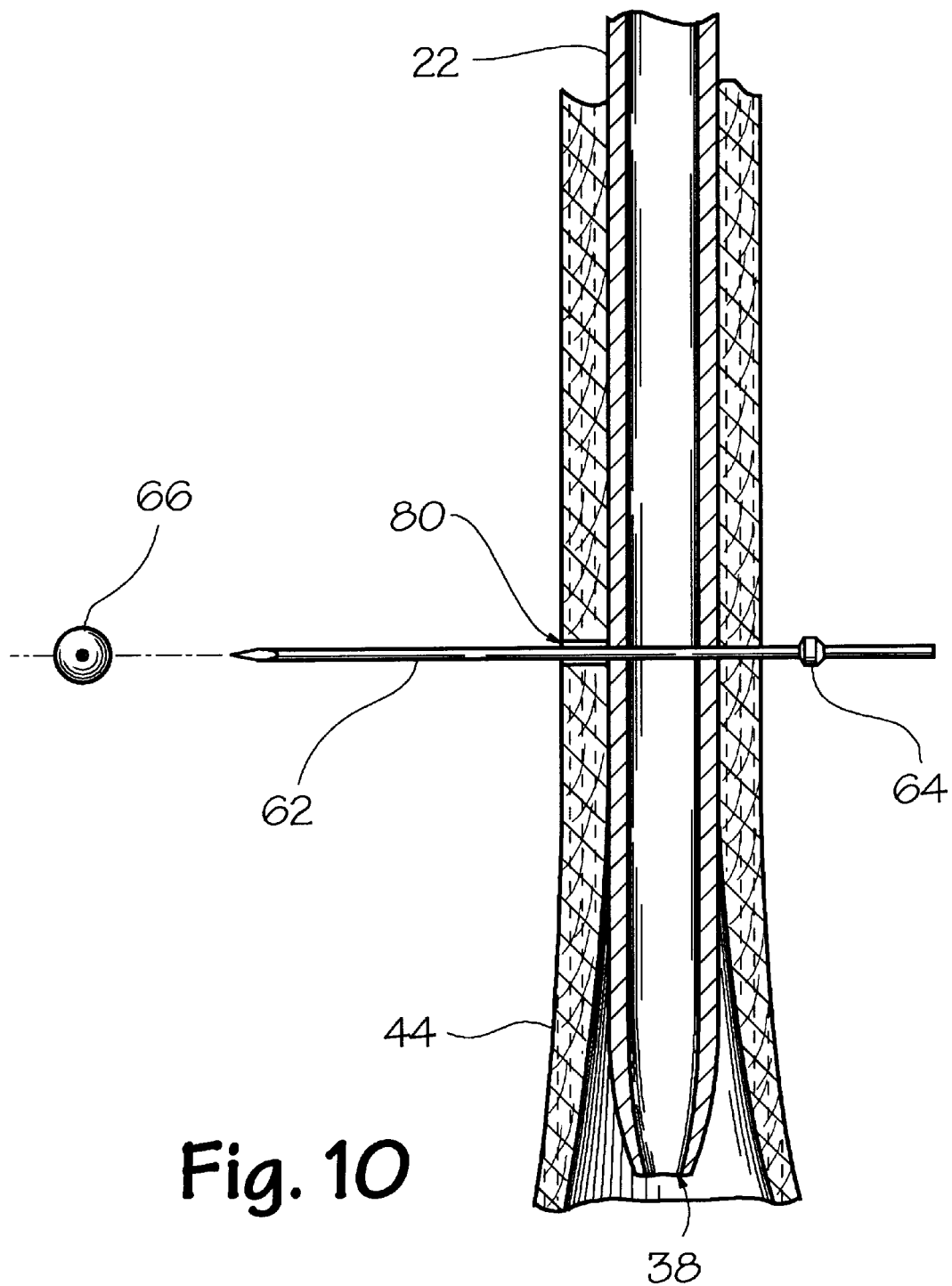
FIG. 10 is a view of the embodiment depicted in FIG. 8 and depicts a next step in the embodiment of FIG. 9.

This interlocking procedure is completed, as shown in FIG. 10, where first sealing plug 24 and first and second sealing plugs 32, 34 have all been removed and Kirschner wire 62 with an associated olive 64 has been passed through from third hole 88 to second hole 84 and first hole 80. A ball 66 is then slipped over the shaft of Kirschner wire 62 and abutted against the outer surface of cortical bone 44 at the site of first hole 80. Kirschner wire 62 is placed under tension to snugly abut olive 64 against the outer surface of cortical bone 44 at the site of third hole 88. The degree of tension depends on the total number of interlocking wires to be used and the weight of the patient, among other factors. The usual range is equivalent from about 30 to 130 kg of weight per interlocking wire. While under tension, with ball 66 snugly abutting cortical 44 at the site of first hole, ball 66 is then permanently affixed to the shaft of Kirschner wire 62 so as to hold the tension on Kirschner wire 62 between olive 64 and ball 66. The free ends of Kirschner wire 62 beyond olive 64 and ball 66 are then trimmed away. In this way, an interlocking wire 58 or 60 has been securely placed through the cortical bone and intramedullary nail.

Figure 11:
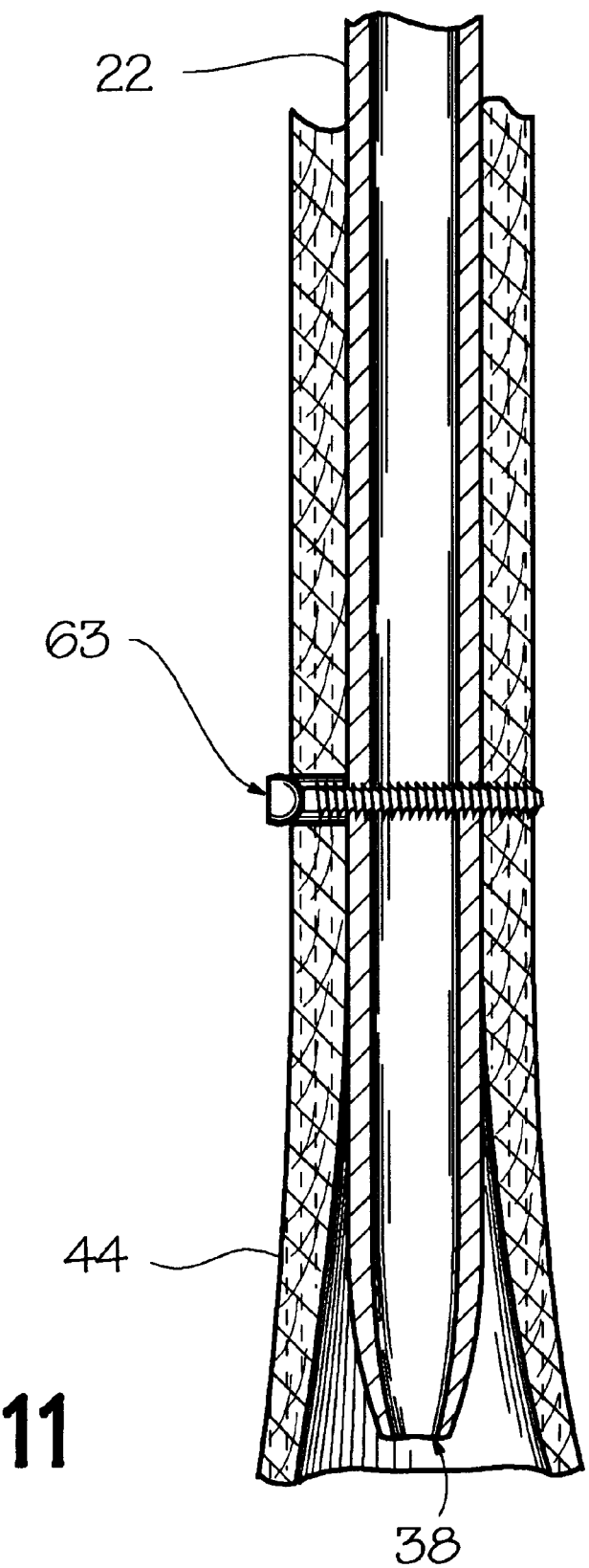
FIG. 11 is a view of an alternate embodiment to that step depicted in FIG. 10.

An alternative interlocking device to a Kirschner wire is depicted in FIG. 11 wherein a cortical screw 63 is chosen having the appropriate diameter and has been passed through hole 80 and is threaded into holes 84 and 88. With the head of cortical screw 63 abutting the outer cortical rim and the threads engaging the opposite cortical side wall, secure interlock is accomplished. This alternative does not require the surgeon to perform a second surgical incision over the opposite cortical bone as is required for passing a Kirschner wire. Additionally, this alternative does not require a tensioning step.

Throughout the various FIGS. 3–13, much of the long bone, including a fracture site, has not been depicted. However, the present invention anticipates the use of intramedullary nail 22 and its associated sealing plugs, resilient stoppers and interlocking wires and screws at any level along the longitudinal axis of the intramedullary nail 22. An additional advantage to the present invention is the ability to place an interlocking device, such as interlocking wires 58 or 60, at the fracture site, particularly, through a loose fracture fragment, such as fracture fragment 52 depicted in FIG. 2. The advantage is the improved stabilization of a comminuted fracture site by locking otherwise loose fracture fragments into their anatomic positions, thus further enhancing the healing process through stabilizing loose fragments. This ability for intramedullary nail device 20 to stabilize loose fragments represents a significant advancement in the approach to treatment and care for severe fractures, such as comminuted fractures of the long bones.

Figure 12:
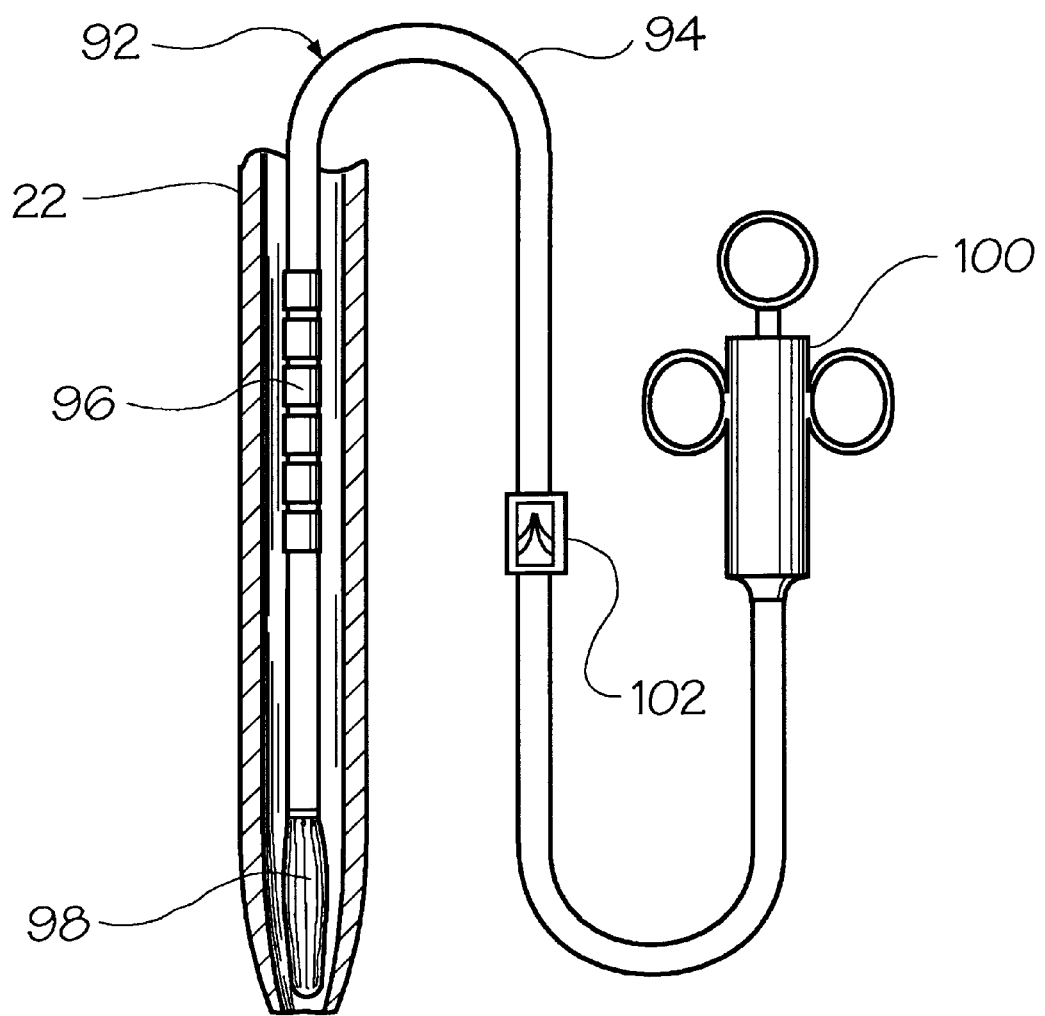
FIG. 12 is a partial sectional view similar to that of FIG. 10 depicting another alternate embodiment of the present invention.
Figure 13:
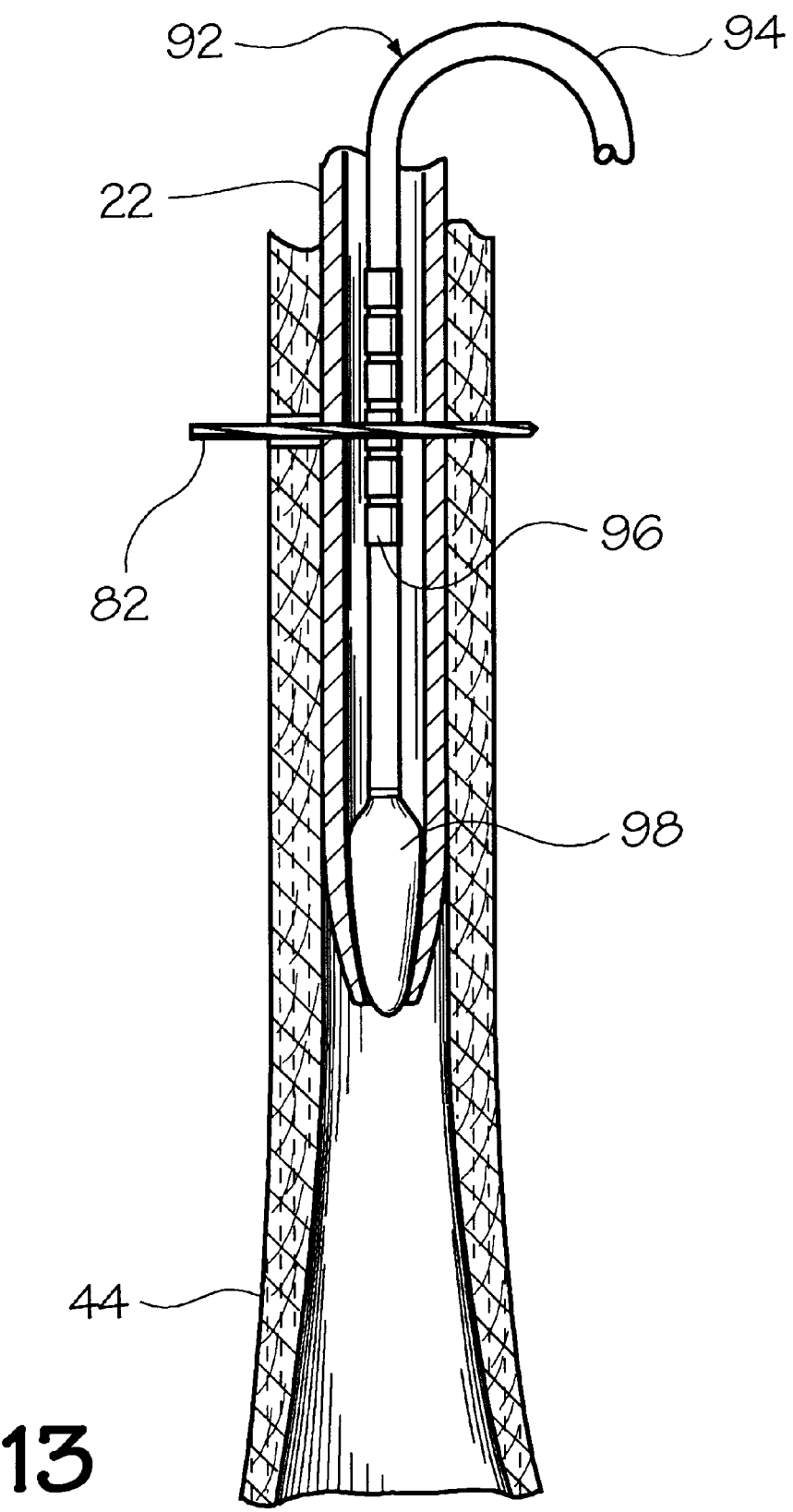
FIG. 13 is a partial sectional view depicting the alternate embodiment depicted in FIG. 11 as the device is positioned with an IM nail.

In FIG. 12, an alternative embodiment of a first sealing plug is depicted as sealing plug subassembly 92 which includes an inflation/deflation tube 94, guard rings 96, distal balloon 98, a pump 100, and a valve 102. As shown in FIG. 12, subassembly 92 is already positioned within the hollow space of IM nail 22 with distal balloon 98 proximate the IM nail distal tip. Valve 102, as part of the tube, is to prevent inadvertent deflation of balloon 98. The alternative is that the surgeon directly cross clamps the tube with some other surgical instrument. Distal balloon 98 is then inflated with pump 100, preferably a syringe attached to the end of tube 94, to provide a seal with balloon 98 against the inner wall of IM nail 22, as depicted in FIG. 13. Debris from drilling is now prevented from escaping through the distal opening of IM nail 22. Guard rings 96 protect tube 94 from inadvertent damage from drill 82 as the drill traverses the hollow center of IM nail 22.

Tube 94 and distal balloon 98 may be constructed with any number of suitable materials ranging from synthetic plastics and rubbers to natural elastic compounds. Biocompatibility is preferable, although not limiting, and a number of materials are known to the art, including polyvinyl chloride, polyurethane, polyethylene, polypropylene, latex and other natural rubbers. The tube and balloon may be manufactured as a single piece with integrated valve, or manufactured as separate components and assembled.

When drill 82 traverses the hollow center, if the drill contacts guard rings 96, the rigid rings deflect tube 94 away from drill 82. Preferably, guard rings 96 are constructed from a material sufficiently rigid withstand the possible pressure that maybe encountered in contacting a drill. The material ideally has a surface that is smooth and has a low coefficient of friction to promote sliding between the drill and the ring. Rigid plastics, rubbers and metals, including stainless steel, are examples of suitable materials for use. Biocompatible compounds are preferred, and are well known in the art. However, this invention anticipates the use many well-known materials suitable for use in subassembly 92. Guard rings 96 are spaced sequentially along tube 94 providing for flexing of tube 94 through the segment of tube 94 bearing guard rings 96.

Following irrigation of the hollow center of IM nail 22, balloon 98 is deflated through tube 96. After placement of an interlocking wire, balloon 98 may then be repositioned more proximally within the hollow center of IM nail 22 to continue with placement of the next interlocking wire, or it may be withdrawn altogether.

Figure 14:
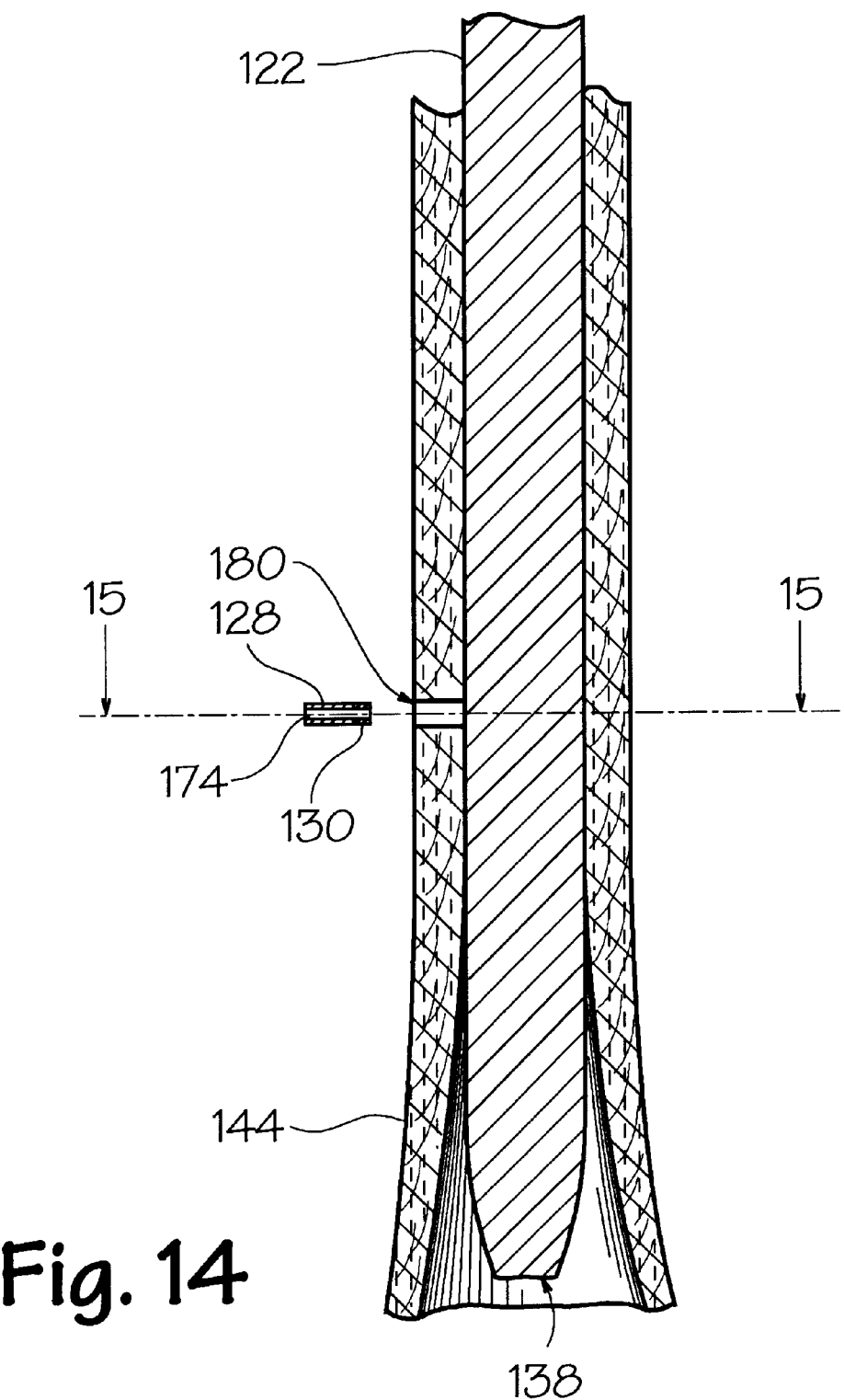
FIG. 14 is a side elevational view of an additional embodiment partial cross-sectional, similar to the view taken at 3—3 of FIG. 1, wherein the more proximal portion of the intramedullary nail and patient's femur is not shown, the view depicting a step in this additional embodiment of the present invention.
Figure 15:
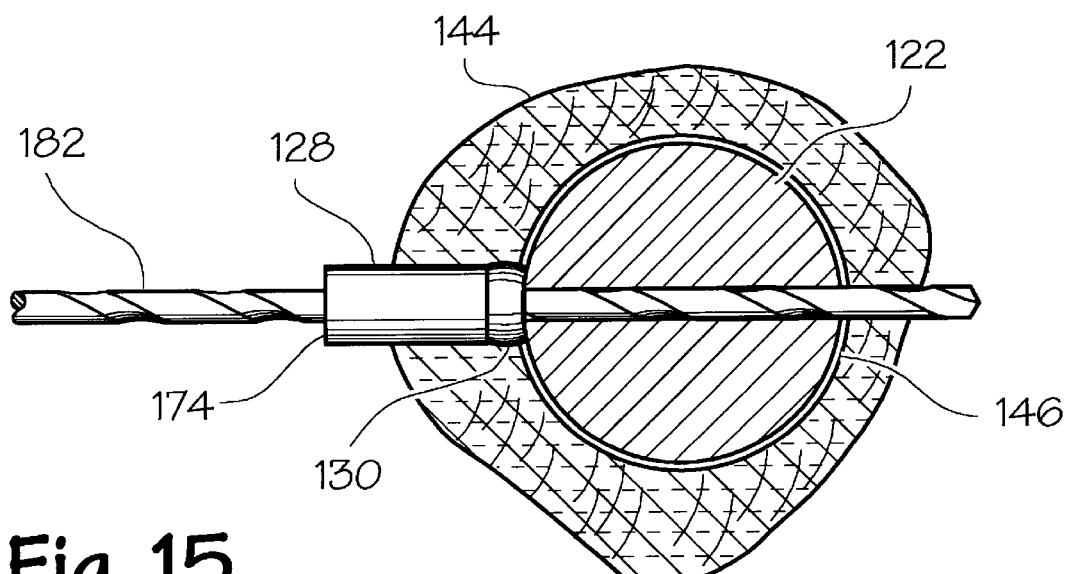
FIG. 15 is a cross-sectional view of the embodiment taken at line 15—15 of FIG. 14 and depicts a next step in the embodiment of FIG. 14.

An alternative embodiment of the present invention is depicted in FIGS. 14–18 showing an IM nail having at least the distal portion of an IM nail 122 as solid. As with the previous embodiment, a hole 180 may be drilled with in the cortical bone 144 of a femur. As shown in FIG. 14, a cylindrical sleeve 128 having a central bore 174, with a resilient gasket 130, is placed into hole 180. The outer diameter of cylindrical sleeve 128 and resilient gasket 130 should very nearly match the internal diameter of hole 180. A close-up cross-sectional view in FIG. 15 demonstrates how a second bit 182 is placed through central bore 174 of cylindrical sleeve 128 and acts as a drill bit guide. Drill bit 182 is then used to drill a second hole 184 (shown in FIG. 16) through the solid core of IM nail 122 and the far wall of cortical bone 144.

Figure 16:
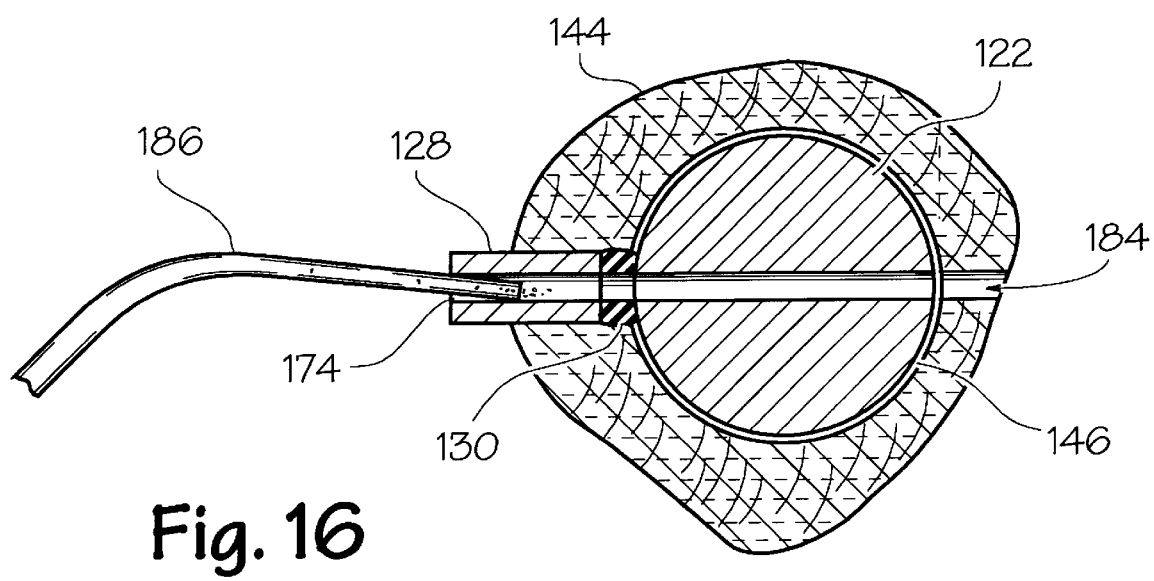
FIG. 16 depicts a next step in the embodiment of FIG. 15.

Irrigation and suction aspiration, as shown in FIG. 16, is carried out with a suction device 186 to completely remove any metallic debris from second hole 184 and central bore 174 prior to removing cylindrical sleeve 28 and resilient gasket 30 from first hole 180. This irrigation and suction step ensures that there will not be any metallic debris left to migrate into medullary space 146 or first hole 180.

Figure 17:
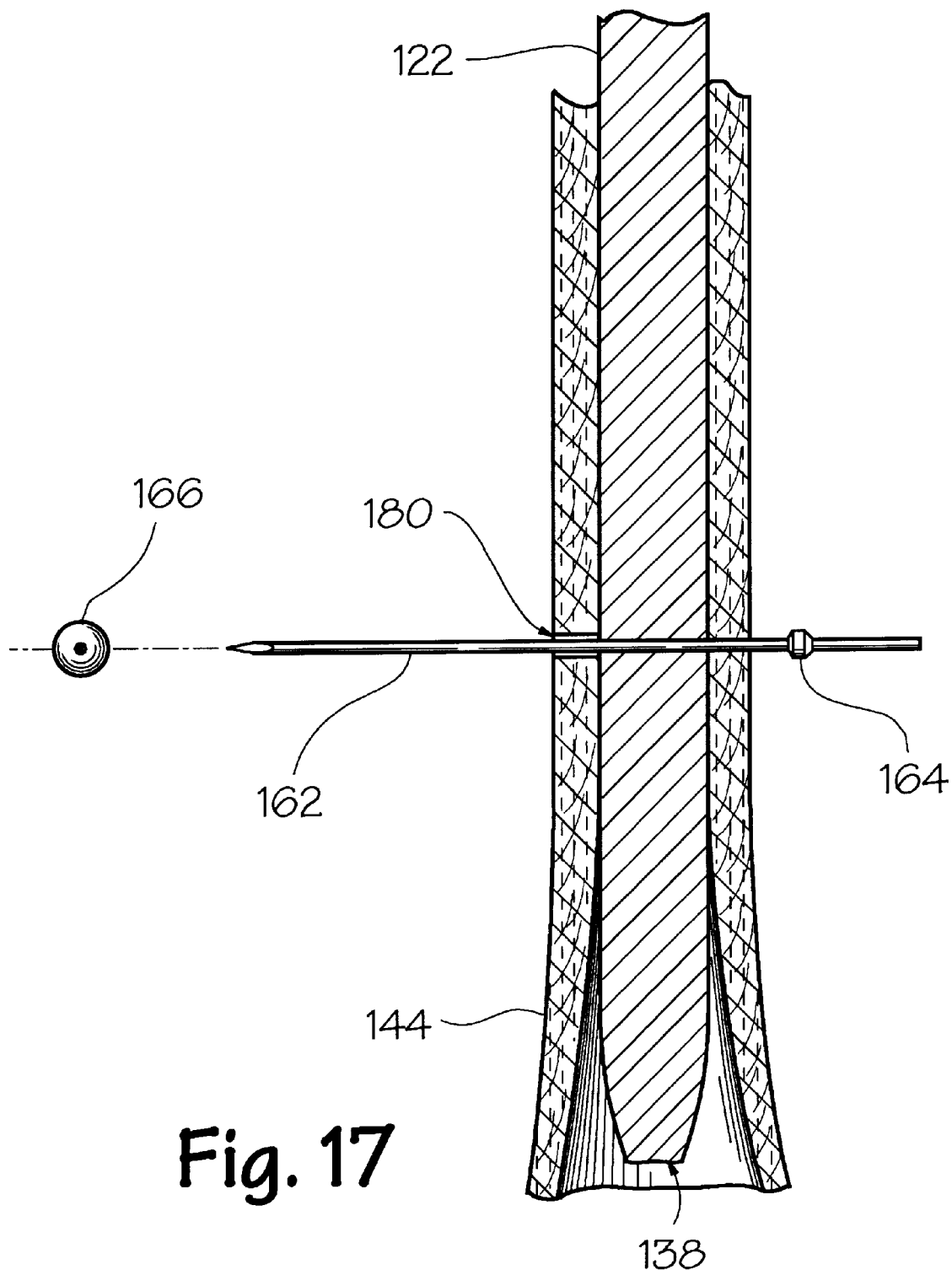
FIG. 17 is a side elevational view of a partial cross-sectional view of a distal aspect of the embodiment of FIG. 14 depicting a next step in the embodiment of FIG. 16.

An interlocking procedure is completed, as shown in FIG. 17, where a Kirschner wire 162 with an associated olive 164 has been passed through hole 184 to first hole 180. A ball 166 is then slipped over the shaft of Kirschner wire 162 and abutted against the outer surface of cortical bone 144 at the site of first hole 180. Kirschner wire 162 is placed under tension to snugly abut olive 64 against the outer surface of cortical bone 144 at the site of hole 184. The degree of tension depends on the total number of interlocking wires to be used and the weight of the patient, among other factors. The usual range is equivalent from about 30 to 130 kg of weight per interlocking wire. While under tension, with ball 166 snugly abutting cortical 144 at the site of first hole, ball 166 is then permanently affixed to the shaft of Kirschner wire 162 so as to hold the tension on Kirschner wire 162 between olive 164 and ball 166. The free ends of Kirschner wire 162 beyond olive 164 and ball 166 are then trimmed away.

Figure 18:
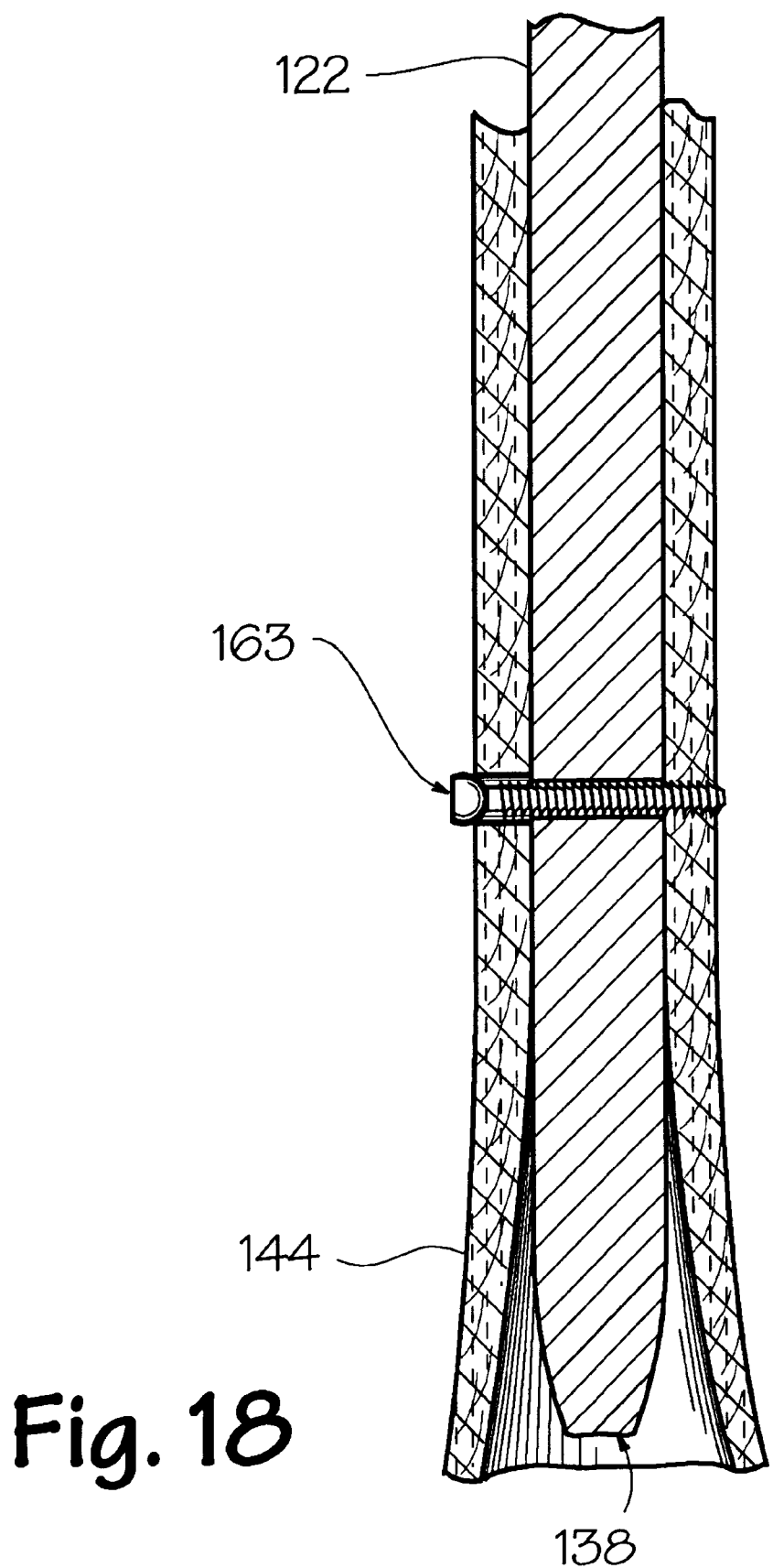
FIG. 18 is a side elevational view of a partial cross-sectional view of a distal aspect of the embodiment of FIG. 14 depicting a next step in the embodiment of FIG. 17.

An alternative interlocking device to a Kirschner wire is depicted in FIG. 18 wherein a cortical screw 163 is chosen, having the appropriate diameter, and has been passed through hole 180 and is threaded into hole 184. With the head of cortical screw 163 abutting the outer cortical rim or cortical bone 144 and the threads engaging the opposite cortical side wall, secure interlock is accomplished. This alternative does not require the surgeon to perform a second surgical incision over the opposite cortical bone as is required for passing a Kirschner wire. Additionally, this alternative does not require a tensioning step.

The foregoing description is considered as illustrative only of the principles of the invention, and since numerous modifications and changes will readily occur to those skilled in the art, it is not the inventor's desire to limit the invention to the exact construction and operation shown and described herein. Accordingly, all suitable modifications and equivalents may be resorted to, falling within the scope of the present invention.

I claim:

1. A method for interlocking an intramedullary nail implantable within a medullary canal of a patient's long bone, the method comprising the steps of:

a) providing an intramedullary nail having an outer wall surface and a longitudinal axis;

b) surgically implanting the intramedullary nail into the medullary canal of the long bone;

c) drilling a first hole through a near wall of the cortical bone using a first drill in a plane substantially transverse to the longitudinal axis and at a selectable longitudinal axial level;

d) providing a cylindrical sleeve having a hollow bore;

e) inserting the cylindrical sleeve into the first hole positioning cylindrical sleeve in operable sealing contact with the outer surface of the near wall of the intramedullary nail;

f) using a second drill, passing through the hollow bore of the cylindrical sleeve, and drilling a second hole through the intramedullary nail and far wall of the cortical bone along the axis of the first hole;

g) irrigating the cylindrical sleeve and second hole with a liquid;

h) suctioning the liquid from the cylindrical sleeve and second hole;

i) removing the cylindrical sleeve;

j) providing an interlocking wire; and k) interlocking the intramedullary nail to the long bone by passing the interlocking wire through the first, second and third holes, tensioning the interlocking wire, and securing the interlocking wire under tension at the outer surfaces of the near and far walls of the cortical bone.

2. The method of claim 1 further comprising the steps of:

l) repeating steps (c) through (k); and m) repeating (m) for a selectable number of iterations.

3. The method of claim 1 in which the intramedullary nail is hollow.

4. The method of claim 3 further comprising the steps of:

e1) providing a removable first sealing plug positionable within the hollow center;

e2) positioning the first sealing plug within the hollow center proximate the distal tip of the nail in operable engagement with the inner wall of the nail;

h1) suctioning and irrigating the hollow center of the intramedullary nail proximally to the first sealing plug; and i1) removing the first sealing plug.

5. The method of claim 4 further comprising the steps of:

l) re-positioning the first sealing plug into the hollow center with the first sealing plug adjacent and proximal to the last placed interlocking wire;

m) repeating steps (c) through (k); and n) repeating (l) and (m) for a selectable number of iterations.

6. The method of claim 3 further comprising the step of providing a removable and expandable second sealing plug in operable sealing contact within the hollow center, positionable to a selectable longitudinal axial second position.

7. The method of claim 1 in which the cylindrical sleeve has a resilient gasket at one end of the sleeve hole and positioning the resilient gasket in operable sealing contact with the outer surface of the near wall of the intramedullary nail.

8. The method of claim 1 in which the intramedullary nail is substantially solid.

9. An intramedullary nail device for implanting within a medullary canal of a long bone of a human, the intramedullary nail device comprising:

a non-fenestrated, non-drilled intramedullary nail elongated along a longitudinal axis and having a hollow center and a proximal opening into the hollow center, the intramedullary nail suitable for providing post implanting drilling there through; and a removable first sealing plug positionable in operable sealing contact within the hollow center to a selectable longitudinal axial first position.

10. The device of claim 9 further comprising:

a cylindrical sleeve having a hollow bore open at both ends on a longitudinal axis, for receiving a drill through the hollow bore, and having a resilient gasket at one end for sealing engagement with the intramedullary nail outer surface, the cylindrical sleeve longitudinal axis in a substantially transverse orientation to the intramedullary nail longitudinal axis;

at least two removable resilient stoppers suitable for placement in at least two holes drillable into the intramedullary nail wall, operably sealing the at least two holes; and interlocking means, passing through the at least two holes drilled into the intramedullary nail, for interlocking the intramedullary nail to the long bone cortex.

11. The device of claim 10 in which the interlocking means includes:

a wire having first stopper means, at a wire first end, for stopping the wire against the long bone cortical surface, and second stopper means, placeable over the wire from a wire second end, for stopping the wire against the long bone cortical surface at a position opposite the first stopper means.

12. The device of claim 11 in which the first stopper means includes a metal bead affixed to the wire.

13. The device of claim 12 in which the first stopper means comprises affixing the metal bead from a selection consisting of: brazing, welding, soldering, or crimping.

14. The device of claim 11 in which the first stopper means includes a metal head formed in the wire toward the first end.

15. The device of claim 11 in which the first stopper means includes a threaded length of the wire at the first end and a nut for threading onto the wire at the first end and operably engaging the long bone cortical surface.

16. The device of claim 15 in which the first stopper means includes a washer for placement over the first end of the wire operably positionable between the nut and the long bone cortical surface.

17. The device of claim 11 in which the second stopper means includes a metal bead for sliding over the wire at the second end and operably crimping to the wire and snugly against the long bone cortical surface.

18. The device of claim 11 in which the second stopper means includes a threaded length of the wire at the second end and a nut for threading onto the wire at the second end for operable engagement of the long bone cortical surface.

19. The device of claim 18 in which the second stopper means includes a washer for placement over the second end of the wire operably positionable between the nut and the long bone cortical surface.

20. A method for interlocking an intramedullary nail implantable within a medullary canal of a patient's long bone, the method comprising the steps of:

a) providing an intramedullary nail having at least a distal portion as a solid core and an outer wall surface and a longitudinal axis;

b) surgically implanting the intramedullary nail into the medullary canal of the long bone;

c) drilling a first hole through a near wall of the cortical bone using a first drill in a plane substantially transverse to the longitudinal axis and at a longitudinal axial level proximate the solid core;

d) providing a cylindrical sleeve having a hollow;

e) inserting the cylindrical sleeve into the first hole to position the resilient gasket in operable sealing contact with the outer surface of the near wall of the intramedullary nail;

f) using a second drill, passing through the cylindrical sleeve, and drilling a second hole through the intramedullary nail and a far wall of the cortical bone opposite the first hole;

g) irrigating the cylindrical sleeve and second hole with a liquid;

h) suctioning the liquid from the cylindrical sleeve and second hole;

i) removing the cylindrical;

j) providing an interlocking wire; and k) interlocking the intramedullary nail to the long bone by passing the interlocking wire through the first and second holes, tensioning the interlocking wire, and securing the interlocking wire under tension at the outer surfaces of the near and far walls of the cortical bone.

21. The method of claim 20 further comprising the step of:

l) repeating steps (c) through (k).

22. The method of claim 21 further comprising the step of:

m) repeating step (l) for a selectable number of iterations.

23. The method of claim 20 in which the cylindrical sleeve has bore and a resilient gasket at one end of the sleeve for operable sealing contact with the outer surface of the intramedullary nail.

24. An intramedullary nail device for implanting within a medullary canal of a long bone of a human, the intramedullary nail device comprising:

a non-fenestrated intramedullary nail, elongated along a longitudinal axis, the intramedullary nail including at least a portion of the distal segment as a solid core adapted for providing post implanting drilling there through of at least two holes; and a cylindrical sleeve having a hollow bore open at both ends on a longitudinal axis, for receiving a drill through the hollow bore, the cylindrical sleeve longitudinal axis operably lying in a substantially transverse orientation to the intramedullary nail longitudinal axis.

25. The intramedullary nail device of claim 24 in which the cylindrical sleeve has a resilient gasket at one end for operable sealing engagement with the intramedullary nail outer surface.

26. The device of claim 25 further comprising:

interlocking means, passing through the at least two holes drilled into the intramedullary nail, for interlocking the intramedullary nail to the long bone cortex.

27. The device of claim 26 in which the interlocking means includes:

a wire having first stopper means, at a wire first end, for stopping the wire against the long bone cortical surface, and second stopper means, placeable over the wire from a wire second end, for stopping the wire against the long bone cortical surface at a position opposite the first stopper means.

28. The device of claim 27 in which the first stopper means includes a metal bead affixed to the wire.

29. The device of claim 28 in which the first stopper means comprises affixing the metal bead from a selection consisting of: brazing, welding, soldering, or crimping.

30. The device of claim 27 in which the first stopper means includes a metal head formed in the wire toward the first end.

31. The device of claim 27 in which the first stopper means includes a threaded length of the wire at the first end and a nut for threading onto the wire at the first end and operably engaging the long bone cortical surface.

32. The device of claim 31 in which the first stopper means includes a washer for placement over the first end of the wire operably positionable between the nut and the long bone cortical surface.

33. The device of claim 27 in which the second stopper means includes a metal bead for sliding over the wire at the second end and operably crimping to the wire and snugly against the long bone cortical surface.

34. The device of claim 27 in which the second stopper means includes a threaded length of the wire at the second end and a nut for threading onto the wire at the second end for operable engagement of the long bone cortical surface.

35. The device of claim 34 in which the second stopper means includes a washer for placement over the second end of the wire operably positionable between the nut and the long bone cortical surface.

* * * * *